(12) United States Patent
Collin et al.

(10) Patent No.: US 10,647,813 B2
(45) Date of Patent: May 12, 2020

(54) PROCESS FOR THE PRODUCTION OF BROMINATED POLYETHER POLYOLS

(71) Applicant: SOLVAY SA, Brussels (BE)

(72) Inventors: Andre Collin, Brussels (BE); Rene Walraevens, Brussels (BE)

(73) Assignee: SOLVAY SA, Brussels (BE)

( * ) Notice: Subject to any disclaimer, the term of this patent is extended or adjusted under 35 U.S.C. 154(b) by 0 days.

(21) Appl. No.: 15/325,216

(22) PCT Filed: Jul. 10, 2015

(86) PCT No.: PCT/EP2015/065806
§ 371 (c)(1),
(2) Date: Jan. 10, 2017

(87) PCT Pub. No.: WO2016/005551
PCT Pub. Date: Jan. 14, 2016

(65) Prior Publication Data
US 2017/0166695 A1   Jun. 15, 2017

(30) Foreign Application Priority Data
Jul. 10, 2014 (EP) .................................... 14176551

(51) Int. Cl.
| | | |
|---|---|---|
| *C08G 65/323* | (2006.01) | |
| *C08G 65/24* | (2006.01) | |
| *C08G 18/50* | (2006.01) | |
| *C08G 18/76* | (2006.01) | |
| *C08G 18/18* | (2006.01) | |
| *C08G 18/40* | (2006.01) | |
| *C08G 18/42* | (2006.01) | |
| *C08G 59/14* | (2006.01) | |
| *C08G 59/30* | (2006.01) | |
| *C08G 59/22* | (2006.01) | |
| *C08G 18/48* | (2006.01) | |
| *C08G 18/66* | (2006.01) | |
| *C08G 18/38* | (2006.01) | |
| *C07C 41/03* | (2006.01) | |
| *C07C 41/22* | (2006.01) | |
| *C07C 43/17* | (2006.01) | |
| *C07C 43/178* | (2006.01) | |
| *C08J 9/12* | (2006.01) | |
| *C08J 9/14* | (2006.01) | |
| *C08G 101/00* | (2006.01) | |

(52) U.S. Cl.
CPC .......... *C08G 65/3233* (2013.01); *C07C 41/03* (2013.01); *C07C 41/22* (2013.01); *C07C 43/17* (2013.01); *C07C 43/1785* (2013.01); *C07C 43/1786* (2013.01); *C08G 18/1816* (2013.01); *C08G 18/381* (2013.01); *C08G 18/4018* (2013.01); *C08G 18/4211* (2013.01); *C08G 18/4829* (2013.01); *C08G 18/4895* (2013.01); *C08G 18/5012* (2013.01); *C08G 18/66* (2013.01); *C08G 18/7671* (2013.01); *C08G 59/1427* (2013.01); *C08G 59/1444* (2013.01); *C08G 59/22* (2013.01); *C08G 59/308* (2013.01); *C08G 65/24* (2013.01); *C08J 9/125* (2013.01); *C08J 9/146* (2013.01); *C08G 2101/00* (2013.01); *C08J 2203/10* (2013.01); *C08J 2203/144* (2013.01); *C08J 2203/182* (2013.01); *C08J 2475/08* (2013.01)

(58) Field of Classification Search
CPC .............. C08G 18/381; C08G 18/4829; C08G 18/5012; C08G 65/24; C08G 65/3233; C08G 18/4895; C08G 59/22; C08G 59/308; C08G 59/1427; C08G 59/1444; C07C 43/17; C07C 43/1785; C07C 43/1786
See application file for complete search history.

(56) References Cited

U.S. PATENT DOCUMENTS

| | | | | |
|---|---|---|---|---|
| 2,792,381 A | * | 5/1957 | Shokal .................. | C08F 220/32 526/273 |
| 4,067,911 A | * | 1/1978 | Walraevens .......... | C07C 43/137 521/171 |
| 4,072,638 A | * | 2/1978 | Boulet ............... | C08G 18/5006 521/126 |
| 4,714,720 A | | 12/1987 | Solvay | |
| 6,406,680 B1 | * | 6/2002 | Priebe ................ | A61K 49/0438 424/9.4 |
| 2004/0085509 A1 | | 5/2004 | Lovelace | |

FOREIGN PATENT DOCUMENTS

| | | | | |
|---|---|---|---|---|
| FR | 2297220 A1 | 8/1976 | | |
| GB | 1353663 A | * | 5/1974 | ........... C07D 303/24 |
| GB | 1371488 A | | 10/1974 | |
| PL | 176952 B1 | * | 8/1999 | |

* cited by examiner

*Primary Examiner* — Kregg T Brooks

(57) ABSTRACT

The present invention relates to brominated polyether polyols, processes for the production as well as intermediates useful in the production of the same and to processes for the preparation of flame-retardant blends, premixes as well as polyurethane foams.

19 Claims, No Drawings

PROCESS FOR THE PRODUCTION OF BROMINATED POLYETHER POLYOLS

This application is a U.S. national stage entry under 35 U.S.C. § 371 of International Application No. PCT/EP2015/065806 filed Jul. 10, 2015, which claims priority to European application No. 14176551.1 filed on Jul. 10, 2014. The entire contents of these applications are explicitly incorporated herein by this reference. The present invention relates to brominated polyether polyols, processes for the production as well as intermediates useful in the production of the same and to processes for the preparation of flame-retardant blends, premixes as well as polyurethane foams.

Polyurethane foams have diverse industrial applications, e.g. in form of insulation panels in the construction industry. They are commonly formed by reacting a di- or polyisocyanate with a polyol. A property of high importance with regard to polyurethane foams is flame-resistance. One way of imparting flame-resistance has been described in U.S. Pat. No. 4,714,720, which describes certain brominated polyetherpolyols, the production of the same and their use in the production of polyurethane foams.

However, there is still a need for improved brominated polyether polyols and for processes of the production of the same.

Now therefore, the invention makes available improved brominated polyether polyols and processes for the production of the same. The process according to this invention is extremely versatile and leads advantageously to compounds or mixtures of compounds with a desired substitution profile. For example, the process according to this invention allows for the introduction of a specific substitution pattern on the brominated polyether polyol. It allows for the introduction not only of alkyl and/or alkoxy side chains but also of chloroalkyl side chains leading to a further improvement in the flame-resistance and other properties, e.g. an improved viscosity. Furthermore, the brominated polyether polyols according to this invention can be prepared with a desired degree of functionalization, i.e. with a desired degree of free hydroxyl groups in the molecule.

Thus, the compounds and processes of the present invention can be fine-tuned in terms of important characteristics for polyether polyols leading advantageously to compounds or mixture of compounds with improved storage stability, viscosity, and/or environmental friendliness. Furthermore, the present invention makes available mixtures of compounds with an improved homogeneity. Additionally, the present invention makes available brominated polyether polyols or mixtures thereof that can be employed to produce polyurethane foams with improved characteristics, especially in terms of their flame-resistance and/or in terms of their dimensional stability.

The processes according to this invention advantageously make available the inventive compounds and/or mixtures of compounds in a technically feasible and economical manner, e.g. in terms of the overall yield, the purity, the energy consumption, the safety requirements, the ease of work-up, and/or the side-product profile.

These advantages and other advantages are achieved by the invention as outlined in the patent claims.

Accordingly, a first embodiment of the present invention concerns a process for the production of a compound or a mixture of compounds according to general formula (I):

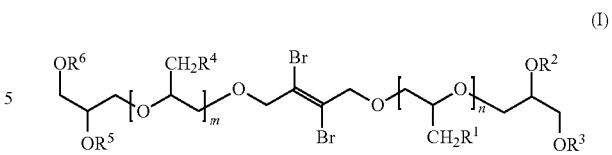

wherein $R^1$ and $R^4$ are independently selected from the group consisting of H, methyl, Cl and Br; $R^2$, $R^3$, $R^5$ and $R^6$ are independently selected from the group consisting of H, methyl, ethyl, propyl and isopropyl; and n and m are independently 0, 1, 2, 3, 4, 5, 6, 7, 8, 9 or 10;
comprising a step wherein a compound or a mixture of compounds of general formula (II):

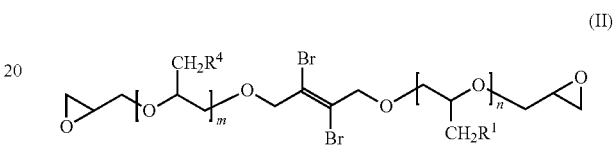

wherein $R^1$, $R^4$, m and n have the meaning as given above; is reacted with water, hydroxide, methanol, methoxide, ethanol, ethoxide, n-propanol, n-propoxide, isopropanol, isopropoxide, or a mixture thereof to obtain the compound or the mixture of compounds of general structure (I); or comprising a step wherein a compound or a mixture of compounds of general formula (III):

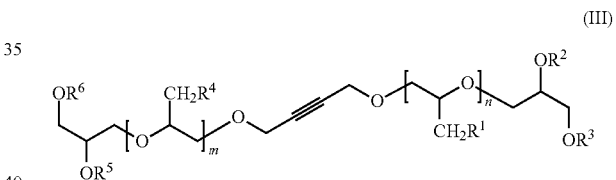

wherein $R^1$, $R^2$, $R^3$, $R^4$, $R^5$, $R^6$, m and n have the meaning as given above; is reacted with bromine, a bromide ion or a bromonium ion, preferably with bromine, to obtain the compound or a mixture of compounds of general structure (I).

Double bonds in all formulas are shown in the trans configuration only. However, this should not be construed as to exclude the compounds in the cis configuration or mixtures of compounds in both cis and trans configuration.

In the first alternative of the first embodiment, the epoxide functionalities of the compound or the mixture of compounds of general formula (II) are reacted with water, hydroxide, methanol, methoxide, ethanol, ethoxide, n-propanol, n-propoxide, isopropanol, isopropoxide, or a mixture thereof. Preferred is a mixture of water and methanol, more preferably a mixture of water and methanol in a weight/weight ratio of 90/10, 80/20, 70/30, 60/40, 50/50, 40/60, 30/70, 20/80 or 10/90. Also preferred is a mixture of water, methanol and ethanol, more preferably a mixture in a weight/weight/weight ratio of 30/60/10, 20/60/20, 20/70/10 or 10/70/20. The reaction can proceed in the presence of at least one additional solvent. The additional solvent is preferably chosen from the group of inert organic solvents, e.g. from ethers, namely tetrahydrofurane, methyl tert-butyl ether or dioxane, halogenated hydrocarbons, namely dichloromethane or 1,2-dichloroethane, hydrocarbons, namely pentanes or hexanes. More preferably, the reaction is performed in the absence of an additional solvent. Additionally, this reaction can be performed in the presence of a catalyst, preferably in the presence of an acid as the catalyst. Preferably, the reaction is performed in the presence of a Lewis acid catalyst. More preferably, the Lewis acid is a metal halogenate, most preferably a metal halogenate of a metal chosen from the $3^{rd}$ main group from the PSE, most preferably the Lewis acid is $BF_3$, $BCl_3$, $AlF_3$ or $AlCl_3$. Also preferably, the reaction is performed in presence of a Brønsted acid. More preferably, the Brønsted acid is a mineral acid; most preferably the Brønsted acid is HCl, HClO, $HClO_2$, $HClO_3$, $HClO_4$, $H_2SO_4$, $H_3PO_4$, HBr or HI. In case the reaction is performed in the presence of an acid catalyst, the reaction mixture is preferably treated with a base after the reaction is completed to neutralize or partially neutralize the reaction mixture. Preferred bases include hydroxides, specifically aqueous sodium hydroxide solutions.

Preferably, the reaction is performed at ambient temperature or at a temperature above ambient, preferably at >25° C., more preferably >40° C., most preferably from 60 to 90° C.

In the second alternative of the first embodiment, the compound or the mixture of compounds of general formula (III) is reacted with bromine, a bromide ion or a bromonium ion, preferably with bromine, to obtain the compound or a mixture of compounds of general structure (I). Preferably, the reaction proceeds in the presence of one or more solvents. The solvents are preferably chosen from the group of organic solvents, e.g. from water, ethers, namely tetrahydrofurane, methyl tert-butyl ether or dioxane, halogenated hydrocarbons, namely dichloromethane or 1,2-dichloroethane, hydrocarbons, namely pentanes or hexanes, alcohols, namely methanol or ethanol, or carboxylic acids, namely acetic acid or propionic acid. The molar ratio of the bromination reagent, preferably the bromine, is chosen to give a ratio of 0.9 to 1.1 mol of bromine per mol of triple bond in the reactant, more preferably 0.95 to 1.05. The temperature of the reaction is preferably ambient or below ambient, preferably at a temperature <20° C., more preferably around 0° C. Also preferably, the reaction temperature is around from 30 to 50° C., more preferably around 40° C. In cases where the reaction conditions allow for the formation of HBr from $Br_2$, for example in a reaction of $Br_2$ with methanol used as a solvent, it can be advantageous to reoxidize the HBr to $Br_2$. Preferably, the reoxidation is performed with $H_2O_2$ or atmospheric oxygen.

In both alternatives of the first embodiment, the reaction is preferably performed in stirred tanks or in autoclaves. The pressure during the reaction is preferably ambient or above ambient. If the pressure is above ambient, the pressure is preferably >1.25 bar, more preferably >1.5 bar, most preferably >1.75 bar. Also preferably, the pressure is <3 bar, more preferably <2 bar.

Any possible solid by-product or contaminant can optionally be removed from the reaction mixture, for example by decanting, filtration and/or centrifugation. Also optionally, any volatiles, e.g. solvents, unreacted reagents or by-products, can be removed from the reaction mixture during or after completion of the reaction. Preferably, these volatiles are removed by distillation, more preferably by distillation under a pressure equal to or below atmospheric pressure, e.g. at a pressure <100 mbar, preferably <50 mbar, and at elevated temperature, preferably at a temperature above 50° C., more preferably above 80° C., most preferably from 90° C. to 120° C.

Optionally, the product can be further purified by methods known to the skilled artisan.

In a preferred embodiment of the first alternative of the first embodiment as described above, the process further comprises a step wherein a compound or a mixture of compounds of general formula (IV):

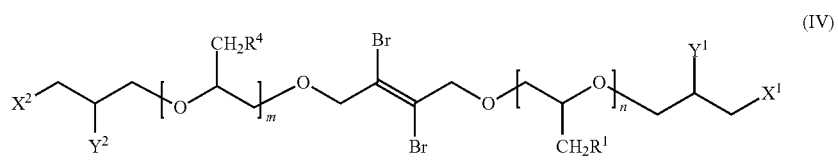

wherein $R^1$ and $R^4$ are independently selected from the group consisting of H, methyl and Cl; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;

is reacted with an acid or a base to obtain the compound or the mixture of compounds of general formula (II).

Preferably, the compound or mixture of compounds of general formula (IV) is reacted with a base, more preferably with a strong Brønsted base, most preferably with a hydroxide, specifically with an aqueous solution of sodium hydroxide.

Preferably, the reaction is performed with molar excess of the base, more preferably with a >10% excess of the base relative to the number of epoxide functionalities to be formed.

Also preferably, the reaction is performed in presence of a Brønsted acid. More preferably, the Brønsted acid is a mineral acid; most preferably the Brønsted acid is HCl, HClO, $HClO_2$, $HClO_3$, $HClO_4$, $H_2SO_4$, $H_3PO_4$, HBr or HI.

The reaction is preferably performed in a stirred tank or in an autoclave. The pressure during the reaction is preferably ambient or below ambient. If the pressure is below ambient, the pressure is preferably <500 mbar, more preferably <350 mbar and >100 mbar. Any possible solid by-product or contaminant can optionally be removed from the reaction mixture, for example by decanting, filtration and/or centrifugation.

Preferably, the reaction proceeds in the presence of one or more solvents. The solvents are preferably chosen from the group of organic solvents, e.g. from ethers, namely tetrahydrofurane, methyl tert-butyl ether or dioxane, halogenated hydrocarbons, namely dichloromethane or 1,2-dichloroethane, hydrocarbons, namely pentanes or hexanes, water, or alcohols, namely methanol or ethanol, or mixtures thereof. More preferable, the reaction is performed in mixture of methanol, water and dichloromethane.

In a further preferred embodiment of the first alternative of the first embodiment as described above, the process further comprises a step wherein a compound or a mixture of compounds of general formula (V):

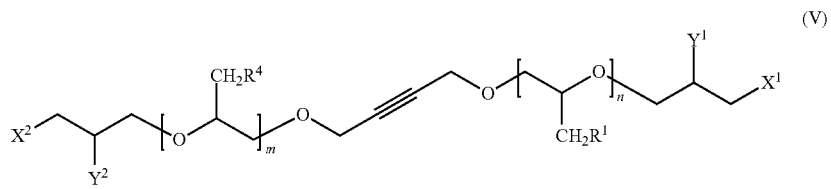

wherein $R^1$ and $R^4$ are independently selected from the group consisting of H, methyl, Cl and Br; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;

is reacted with bromine, a bromide ion or a bromonium ion, preferably with bromine, to obtain the compound or the mixture of compounds of general formula (IV). The bromination reaction according to this embodiment is preferably performed as described above for the second alternative of the first embodiment [formula (III) to formula (II)].

In a further preferred embodiment of the first alternative of the first embodiment as described above, the process further comprises a step wherein epichlorohydrin is reacted with but-2-yne-1,4-diol to obtain the compound or the mixture of compounds of general formula (V), more preferably epichlorohydrin is reacted with but-2-yne-1,4-diol in presence of an acid or a base, more preferably in presence of an acid. Even more preferably, the acid can be chosen from the list of acids as described in the first alternative of the first embodiment. Preferably, the reaction proceeds in the presence of one or more solvents. The solvents are preferably chosen from the group of organic solvents, e.g. from ethers, namely tetrahydrofurane, methyl tert-butyl ether or dioxane, halogenated hydrocarbons, namely dichloromethane or 1,2-dichloroethane, hydrocarbons, namely pentanes or hexanes, water, or alcohols, namely methanol or ethanol, or mixtures thereof. Also preferably, the reaction is performed in the absence of an additional solvent.

The reaction is preferably performed at a temperature above ambient, more preferably from 45 to 90° C. The molar ratio of epichlorohydrin or epibromohydrin to but-2-yne-1, 4-diol is chosen from 5:1 to 1:5, preferably from 3:1 to 1:1, more preferably from 3:1 to 2:1, specifically around 2.5:1.

In a preferred embodiment of the second alternative of the first embodiment as described above, the process comprises a further step wherein a compound or a mixture of compounds of general formula (VI):

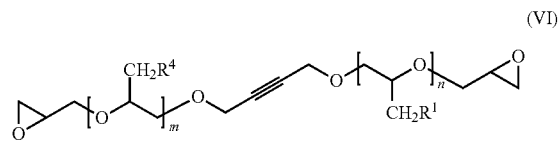

wherein $R^1$ and $R^4$ are independently selected from the group consisting of H, methyl, Cl and Br; and n and m are independently 0, 1, 2, 3, 4, 5, 6, 7, 8, 9 or 10;

is reacted with water, hydroxide, methanol, methoxide, ethanol, ethoxide, n-propanol, n-propoxide, isopropanol, isopropoxide, or a mixture thereof to obtain the compound or the mixture of compounds of general structure (III). Preferably, this further step is performed as described for the analogues reaction [formula (II) to formula (I)] in the first alternative of the first embodiment as described above.

In a further preferred embodiment of the second alternative of the first embodiment as described above, the process comprises a further step wherein a compound or a mixture of compounds of general formula (V):

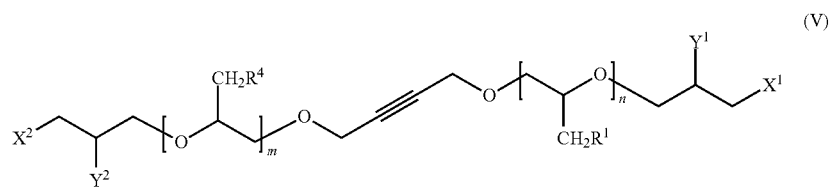

wherein $R^1$ and $R^4$ are independently selected from the group consisting of H, methyl, Cl and Br; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;

is reacted with an acid or a base to obtain the compound or the mixture of compounds of general formula (VI). Preferably, this further step is performed as described for the analogues reaction [formula (IV) to formula (II)] in the preferred embodiment of the first alternative of the first embodiment as described above.

In a further preferred embodiment of the second alternative of the first embodiment as described above, the process further comprises a step wherein epichlorohydrin is reacted with but-2-yne-1,4-diol to obtain the compound or the mixture of compounds of general formula (V), more preferably epichlorohydrin is reacted with but-2-yne-1,4-diol in presence of an acid or a base, more preferably in presence of an acid. Preferably, this further step is performed as described for the same reaction in the preferred embodiment of the first alternative of the first embodiment as described above.

In an another preferred embodiment of the first alternative of the first embodiment, the process comprises a further step wherein 2,3-dibromo-but-2-ene-1,4-diol is reacted with epichlorohydrin to yield a compound or a mixture of compounds of general structure (IV). Preferably, the reaction is performed as described above for the reaction of epichlorohydrin with but-2-yne-1,4-diol above.

The intermediates of any of the processes as described above can optionally be purified before the next reaction step. Preferably, they are used without further purification.

A second embodiment of the present invention concerns a compound or a mixture of compounds of general formula (I):

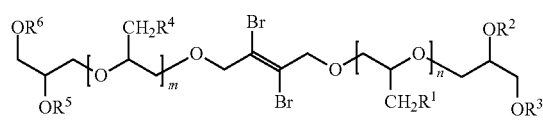
(I)

wherein $R^1$ and $R^4$ are independently selected from the group consisting of H, methyl, Cl, and Br; $R^2$, $R^3$, $R^5$ and $R^6$ are independently selected from the group consisting of H, methyl, ethyl, propyl and isopropyl; and n and m are independently 0, 1, 2, 3, 4, 5, 6, 7, 8, 9 or 10;

general formula (II):

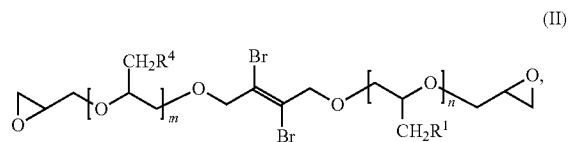
(II)

wherein $R^1$ and $R^4$ are independently selected from the group consisting of H, methyl, Cl and Br; n and m are independently 0, 1, 2, 3, 4, 5, 6, 7, 8, 9 or 10;

general formula (III):

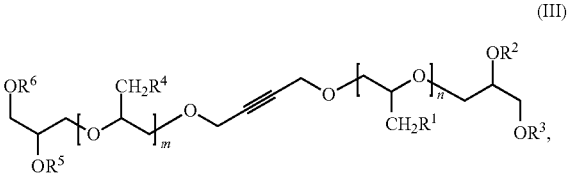
(III)

wherein $R^1$ and $R^4$ are independently selected from the group consisting of H, methyl, Cl and Br; $R^2$, $R^3$, $R^5$ and $R^6$ are independently selected from the group consisting of H, methyl, ethyl, propyl and isopropyl; n and m are independently 0, 1, 2, 3, 4, 5, 6, 7, 8, 9 or 10;

general formula (IV):

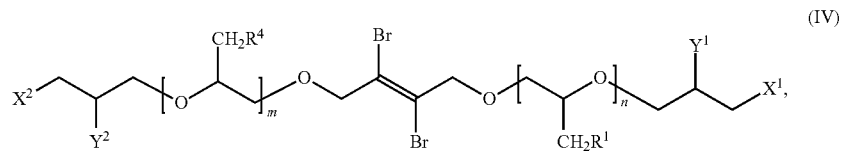
(IV)

wherein $R^1$ and $R^4$ are independently selected from the group consisting of H, methyl, Cl and Br; n and m are independently 0, 1, 2, 3, 4, 5, 6, 7, 8, 9 or 10; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH;

general formula (V):

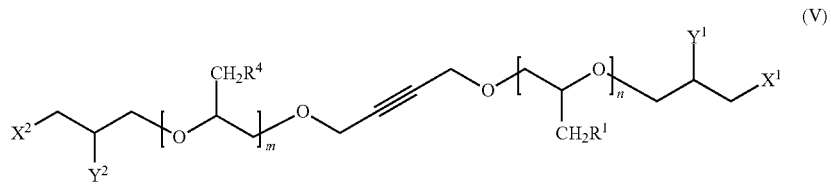

wherein $R^1$ and $R^4$ are independently selected from the group consisting of H, methyl, Cl and Br; n and m are independently 0, 1, 2, 3, 4, 5, 6, 7, 8, 9 or 10; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH;

or general formula (VI):

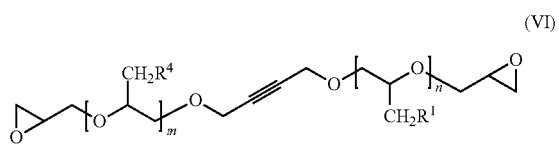

wherein $R^1$ and $R^4$ are independently selected from the group consisting of H, methyl, Cl and Br; n and m are independently 0, 1, 2, 3, 4, 5, 6, 7, 8, 9 or 10; as well as their use as flame retardant and/or their use in the manufacture of flame retardants.

In a preferred embodiment of the process as well as the compound or the mixture of compounds according to this invention, $R^1$ and $R^4$ are Cl. In another preferred embodiment of the process and as well as the compound or the mixture of compounds according to this invention, $R^2$, $R^3$, $R^5$ and $R^6$ are independently selected from H and methyl. In yet another preferred embodiment of the process and as well as the compound or the mixture of compounds according to this invention, m is 0.

In a most preferably embodiment of the process as well as the compound or the mixture of compounds according to this invention, m is 0, $R^1$ is Cl, and $R^2$, $R^3$, $R^5$ and $R^6$ are independently selected from H and methyl.

A third embodiment of the present invention concerns a process for the preparation of a flame-retardant blend comprising a step of blending the product of a process or a compound or a mixture of compounds according to this invention with a further flame-retardant. Any flame retardant conventionally used in the manufacture of such foams can be used. Mention may be made, for example, of triethyl phosphate, trischloroisopropyl phosphate and other phosphates or phosphonates. Most preferably, triethyl phosphate is used.

A fourth embodiment of the present invention concerns a process for the preparation of a premix comprising a step of blending the product of a process or a compound or a mixture of compounds according to this invention and/or the flame-retardant blend according to this invention with a blowing agent and optionally on or more further components selected from the list consisting of further polyol compounds, foam stabilizer, further blowing agents, further flame retardants, catalysts, cross-linking agents and surfactants.

Suitable polyols include any conventionally used polyether and/or polyester polyol.

Suitable surfactants are known in the art, silica-based surfactants are preferred, e.g. Struksilon® 8006 (Schill+Seilacher "Struktol" GmbH).

Suitable cross-linking agents are known in the art, e.g. hydroxyl-substituted amine like triethanolamine.

Suitable catalysts are known in the art, e.g. tertiary amines and organic tin, iron, mercury or lead compounds. Mention may in particular by made, as tertiary amines, of triethylamine, N,N dimethylcyclohexylamine, N-methylmorpholine, N-ethylmorpholine, dimethylethanolamine, diaza[2.2.2]bicyclooctane (triethylenediamine) and substituted benzylamines, such as N,N-dimethylbenzylamine. Mention may in particular be made, as organic tin or lead compounds, of dibutyltin dilaurate, stannous octanoate and lead octanoate. Other suitable catalysts intended for the manufacture of modified polyurethane (polyisocyanurate) foams include compounds that catalyse the trimerization of isocyanates to triisocyanurates.

Any foam stabilizer conventionally used in the manufacture of such foams can be used. Mention may be made, for example, of siloxane polyether copolymers.

Any blowing agent mixture conventionally used in the manufacture of such foams can be used. Mention may be made, for example, of water, isomers of pentanes, specifically n-pentane, isopentane, neopentane or mixture thereof, 1,1,1,3,3-pentafluorobutane (HFC 365mfc), 1,1,1,2-tetrafluoroethane (HFC-134a), 1,1,1,2,3,3,3-heptafluoropropane (HFC 227ea), 1,1,1,3,3-pentafluorpropane (HFC 245fa), halogenated olefins like HFO-1234yf, HFO-1234zr and HFO-1233zd, or mixtures of said alkanes and alkenes. Preferred are mixtures of HFC 365mfc and HFC 245fa, especially a mixture of 70:30 of HFC 365mfc and HFC 245fa and mixtures of HFC 365mfc and HFC 227ea, especially the mixtures of 93:07 or 87:13 of HFC 365mfc and HFC 227ea.

A fourth embodiment of the present invention concerns a process for the preparation of a polyurethane foam comprising a step of reacting the product of a process according to this invention or a compound, a mixture of compounds, a premix or a flame-retardant blend according to this invention with one or more isocyanate compounds.

Any isocyanate conventionally used to manufacture such foams can be used in the process according to the invention. Mention may be made, by way of example, of aliphatic isocyanates, such as hexamethylene diisocyanate, and aromatic isocyanates, such as tolylene diisocyanate or diphenylmethane diisocyanate.

Should the disclosure of any of the patents, patent applications, and publications that are incorporated herein by reference be in conflict with the present description to the extent that it might render a term unclear, the present description shall take precedence.

EXAMPLES

Example 1a

Condensation with Brønsted Acid

A reactor is charged with 2.0 kg but-2-yne-1,4-diol. The reactor is heated by pumping water at 95° C. through the heating coils. At an inner temperature of 90° C., stirring is started and 2.7 g 65% $HClO_4$ is added to the melted but-2-yne-1,4-diol followed by the addition of 5.3 kg epichlorohydrin over the course of 300 min. During the addition, the temperature is maintained at 90° C. Subsequently, the mixture is cooled to 65° C. and 1.3 kg methanol is added to allow transferring the crude reaction mixture to the reactor for the next reaction step.

Example 1b

Condensation with Lewis Acid

A reactor is charged with 2.0 kg but-2-yne-1,4-diol. The reactor is heated by pumping water at 95° C. through the heating coils. At an inner temperature of 80° C., stirring is started and 4.0 g $BF_3 \cdot OEt_2$ is added to the melted but-2-yne-1,4-diol. The temperature is raised to 90° C. followed by the addition of 5.3 kg epichlorohydrin over the course of 300 min. During the addition, the temperature is maintained at 90° C. Subsequently, the mixture is cooled to 65° C. and 1.3 kg methanol is added to allow transferring the crude reaction mixture to the reactor for the next reaction step.

Example 1c

Condensation with Base

A reactor is charged with 2.0 kg but-2-yne-1,4-diol. The reactor is heated by pumping water at 95° C. through the heating coils. At an inner temperature of 90° C., stirring is started and 5.3 g KOH pellets is added to the melted but-2-yne-1,4-diol. The mixture is stirred for 30 min followed by the addition of 5.3 kg epichlorohydrin over the course of 300 min. During the addition, the temperature is maintained at 90° C. Subsequently, the mixture is cooled to 65° C. and 1.3 kg methanol is added to allow transferring the crude reaction mixture to the reactor for the next reaction step.

Example 2a

Bromination Procedure 1

The crude mixture from example 1a, 1b or 1c as well as 1.0 mol-equivalents $Br_2$ are fed to a stirred reactor simultaneously at a rate allowing the internal temperature in the reactor to be around 49° C. After complete addition of $Br_2$ (usually around 3 h), 0.13 kg of a 35% $H_2O_2$ solution is added to the mixture over the course of 40 min. Subsequently, the mixture is allowed to cool and directly used for the next step.

Example 2b

Bromination Procedure 2

The crude mixture from example 1a, 1b or 1c is placed in a stirred reactor. To this mixture, 1.0 mol-equivalents $Br_2$ and 0.13 kg of a 35% $H_2O_2$ solution are fed simultaneously at a rate allowing the internal temperature in the reactor to be around 19° C. After complete addition of the $H_2O_2/Br_2$ mixture (usually around 1.5 h), the reaction mixture is allowed to cool to room temperature and directly used for the next step.

Example 3a

Epoxidation with Strong Base

A reactor is charged with the mixture from example 2a or 2b and 1.2 kg dichloromethane. 1.5 kg of a 50% aqueous solution of NaOH is fed to the reaction mixture at a rate so as to maintain the internal temperature at 45° C. After stirring for another 40 min, 2.5 kg water is added and the mixture is stirred for another 20 min. After decanting, the two phases formed are separated and the organic phase is directly used for the next step.

Example 3b

Epoxidation with Strong Acid

A reactor is charged with the mixture from example 2a or 2b and 1.2 kg dichloromethane. To this mixture, 0.73 kg concentrated $H_2SO_4$ is added slowly and the internal temperature is subsequently raised to 65° C. After stirring at this temperature for 90 min, the mixture is neutralized by addition of 20% aqueous NaOH solution. The mixture is stirred for another 10 min and subsequently decanted. The two phases formed are separated and the organic phase is directly used for the next step.

Example 4a

Ring Opening Procedure 1

A stirred reactor equipped with a condenser is charged with 5.5 kg crude product from example 3a or 3b. A mixture of 1.2 kg methanol, 2.1 kg water, 1.2 kg ethanol and 0.02 kg concentrated HCl is added. The reactor is heated to 85° C. and the reaction mixture is stirred under reflux conditions for 60 min. The mixture is allowed to cool to room temperature and neutralized by addition of 20% aqueous NaOH solution. After decanting from the solids formed, the volatiles are removed by evaporation at 90° C. under vacuum (300 to 30 mbar) to yield the desired product.

Example 4b

Ring-Opening Procedure 2

An autoclave is charged with 1.3 kg methanol, 3.3 kg water and 0.02 kg 65% $HClO_4$. The autoclave is kept at a pressure of 1.9 bar and heated to 65° C., after which 5.5 kg of the crude product from example 3a or 3b is added. During the addition, the temperature is allowed to rise to 75° C. After complete addition, the temperature is raised to 85° C. and the reaction is allowed to stir for another 30 min. The reaction mixture is neutralized by addition of 20% aqueous NaOH solution. The volatiles are removed by evaporation at 90° C. under vacuum (300 to 30 mbar) to yield the desired product.

Example 5a

Epoxidation with Strong Base

A reactor is charged with the mixture from example 1a, 1b or 1c and 1.2 kg dichloromethane. 1.5 kg of a 50% aqueous solution of NaOH is fed to the reaction mixture at a rate so as to maintain the internal temperature at 45° C. After stirring for another 40 min, 2.5 kg water is added and the mixture is stirred for another 20 min. After decanting, the two phases formed are separated and the organic phase is directly used for the next step.

Example 5b

Epoxidation with Strong Acid

A reactor is charged with the mixture from example 1a, 1b or 1c and 1.2 kg dichloromethane. To this mixture, 0.73 kg concentrated $H_2SO_4$ is added slowly and the internal temperature is subsequently raised to 65° C. After stirring at this temperature for 90 min, the mixture is neutralized by addition of 20% aqueous NaOH solution. The mixture is stirred for another 10 min and subsequently decanted. The two phases formed are separated and the organic phase is directly used for the next step.

Example 6a

Ring Opening Procedure 1

A stirred reactor equipped with a condenser is charged with 5.5 kg crude product from example 5a or 5b. A mixture of 1.2 kg methanol, 2.1 kg water, 1.2 kg ethanol and 0.02 kg concentrated HCl is added. The reactor is heated to 85° C. After the dichloromethane from the previous step is distilled off, the reaction mixture is stirred under reflux conditions for 60 min. The mixture is allowed to cool to room temperature and neutralized by addition of 20% aqueous NaOH solution.

Example 6b

Ring-Opening Procedure 2

An autoclave is charged with 1.3 kg methanol, 3.3 kg water and 0.02 kg 65% $HClO_4$. The autoclave is kept at a pressure of 1.9 bar and heated to 65° C., after which 5.5 kg of the crude product from example 3a or 3b is added. During the addition, the temperature is allowed to rise to 75° C. After complete addition, the temperature is raised to 85° C. and the reaction is allowed to stir for another 30 min. The reaction mixture is neutralized by addition of 20% aqueous NaOH solution and decanted from the solids formed.

Example 7a

Bromination Procedure 1

The crude mixture from example 6a or 6b as well as 1.05 mol-equivalents $Br_2$ dissolved in 1.0 kg dichloromethane (optionally recycled from the previous step) are fed to a stirred reactor simultaneously at a rate allowing the internal temperature in the reactor to be around 49° C. After complete addition of the $Br_2$ solution (usually around 3 h), 0.13 kg 35% $H_2O_2$ solution is added to the mixture over the course of 40 min. After cooling to room temperature and decanting, the phases are separated. To the organic phase, 0.5 kg water is added and the mixture is stirred for 15 min. The phases are separated and the organic phase is evaporated at 90° C. under vacuum (300 to 30 mbar) to yield the desired product.

Example 7b

Bromination Procedure 2

The crude mixture from example 6a or 6b as well as 1.0 kg dichloromethane (optionally recycled from the previous step) are placed in a stirred reactor. To this mixture, 1.05 mol-equivalents $Br_2$ and 0.13 kg 35% $H_2O_2$ solution are fed simultaneously at a rate allowing the internal temperature in the reactor to be around 19° C. After complete addition of the $H_2O_2/Br_2$ mixture (usually around 1.5 h), the mixture is cooled to room temperature and decanted. The phases are separated. To the organic phase, 0.5 kg water is added and the mixture is stirred for 15 min. The phases are separated and the organic phase is evaporated at 90° C. under vacuum (300 to 30 mbar) to yield the desired product.

Example 8

Preparation of a Premix

A premix was prepared by blending the following components using conventional means:

| Compound | Type | Part by weight |
|---|---|---|
| Product of example 4a, 4b, 7a or 7b | | 6 |
| Stepanpol ® PS2412 | Aromatic Polyester polyol | 45 |
| Voranol ® RN490 | Polyether polyol | 30 |
| TEP | Physical flame retardant | 5 |
| DMCHA | Amine based catalyst | 2.3 |
| Struksilon ® 8006 | Surfactant | 1.5 |
| Solkane ® 365 | Blowing agent (physical) | 18.4 |
| Water | Blowing agent (chemical) | 1.4 |

Voranol ® RN 490 (Dow chemicals), Struksilon ® 8006 (Schill + Seilacher "Struktol" GmbH), triethylphosphat (TEP), Stepanpol ® PS 2412, HFC 365mfc (Solkane ® 365) and 1 wt % N,N-dimethylcyclohexylamine (DMCHA, Lupragen ® N100).

Example 9

Preparation of a Polyurethane Foam

A polyurethane foam was prepared by conventional means using the premix from example 8 and

| Compound | Type | Part by weight |
|---|---|---|
| Methylendiphenyldiisocyanat (MDI) | Isocyanate | 143.4 |

An isocyanate MDI index of 115 was applied to prepare the polyurethane foams.

The invention claimed is:

1. A process for the production of a compound or a mixture of compounds according to general formula (I):

$$\begin{array}{c}\text{(I)}\\ \text{OR}^6 \quad \text{CH}_2\text{R}^4 \quad \text{Br} \quad \text{OR}^2\\ \diagdown\text{O}\diagup_m\text{O}\diagup\diagup\text{O}\diagup_n\diagdown\\ \text{OR}^5 \quad \text{Br} \quad \text{CH}_2\text{R}^1 \quad \text{OR}^3\end{array}$$

wherein $R^1$ and $R^4$ are independently selected from the group consisting of H, methyl, Cl and Br; $R^2$, $R^3$, $R^5$ and $R^6$ are independently selected from the group consisting of H, methyl, or ethyl; and n and m are independently 0, 1, 2, 3, 4, 5, 6, 7, 8, 9 or 10;

the process comprising a step wherein a compound or a mixture of compounds of general formula (II):

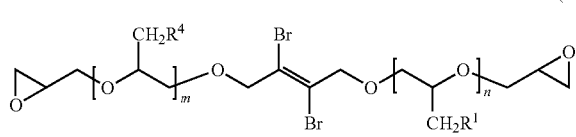

wherein $R^1$, $R^4$, m and n have the meaning as given above;
is reacted with a mixture of water and methanol in a weight/weight ratio of 90/10, 80/20, 70/30, 60/40, 50/50, 40/60, 30/70, 20/80 or 10/90; or a mixture of water, methanol, and ethanol in a weight/weight/weight ratio of 30/60/10, 20/60/20, 20/70/10 or 10/70/20 to obtain the compound or the mixture of compounds of general structure (I);
or
comprising a step wherein a compound or a mixture of compounds of general formula (III):

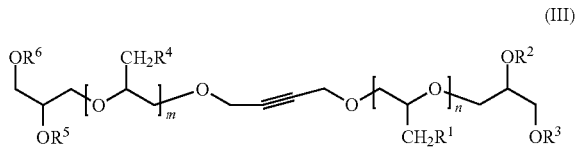

wherein $R^1$, $R^2$, $R^3$, $R^4$, $R^5$, $R^6$, m and n have the meaning as given above;
is reacted with bromine, a bromide ion or a bromonium ion, to obtain the compound or a mixture of compounds of general structure (I); and obtaining the compound or the mixture of compounds of general structure (III) in a step wherein a compound or a mixture of compounds of general formula (VI):

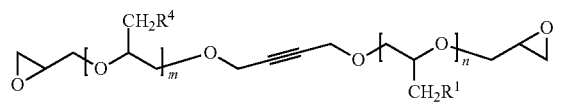

wherein $R^1$ and $R^4$ are independently selected from the group consisting of H, methyl, Cl and Br; and n and m are independently 0, 1, 2, 3, 4, 5, 6, 7, 8, 9 or 10;

is reacted with a mixture of water and methanol in a weight/weight ratio of 90/10, 80/20, 70/30, 60/40, 50/50, 40/60, 30/70, 20/80 or 10/90; or a mixture of water, methanol and ethanol in a weight/weight/weight ratio of 30/60/10, 20/60/20, 20/70/10 or 10/70/20.

2. The process according to claim 1 comprising the step wherein the compound or the mixture of compounds of general formula (II):

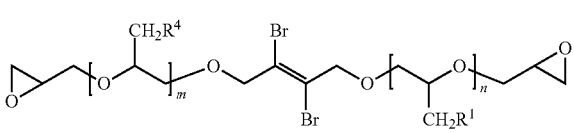

wherein $R^1$ and $R^4$ are independently selected from the group consisting of H, methyl, Cl and Br; and n and m are independently 0, 1, 2, 3, 4, 5, 6, 7, 8, 9 or 10
is reacted with a mixture of water and methanol in a weight/weight ratio of 90/10, 80/20, 70/30, 60/40, 50/50, 40/60, 30/70, 20/80 or 10/90; or a mixture of water, methanol, and ethanol in a weight/weight/weight ratio of 30/60/10, 20/60/20, 20/70/10 or 10/70/20, to obtain the compound or the mixture of compounds of general structure (I);
and further comprising obtaining the compound or the mixture of compounds of general formula (II) in a step wherein a compound or a mixture of compounds of general formula (IV):

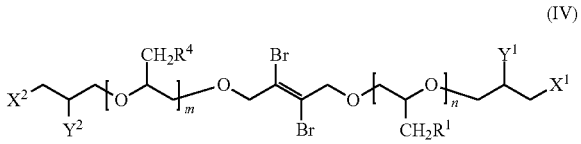

wherein $R^1$ and $R^4$ are independently selected from the group consisting of H, methyl and Cl; $X^1$, $X^2$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;
is reacted with an acid or a base.

3. The process according to claim 2 further comprising obtaining the compound or the mixture of compounds of general formula (IV) in a step wherein a compound or a mixture of compounds of general formula (V):

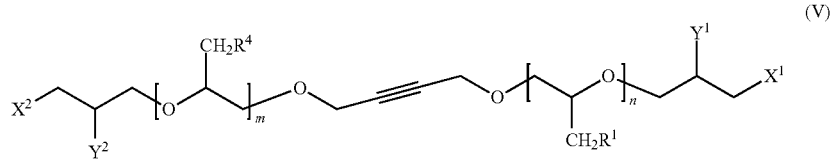

wherein $R^1$ and $R^4$ are independently selected from the group consisting of H, methyl, Cl and Br; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;

is reacted with bromine, a bromide ion or a bromonium ion.

4. The process according to claim 3 further comprising obtaining the compound or the mixture of compounds of general formula (V) in a step wherein epichlorohydrin is reacted with but-2-yne-1,4-diol.

5. The process according to claim 4 wherein epichlorohydrin is reacted with but-2-yne-1,4-diol in presence of an acid or a base.

6. The process according to claim 5 wherein epichlorohydrin is reacted with but-2-yne-1,4-diol in presence of an acid.

7. The process of claim 3, wherein the compound or the mixture of compounds of general formula (V) is reacted with bromine.

8. The process according to claim 1 further comprising obtaining the compound or the mixture of compounds of general formula (VI) in a step wherein a compound or a mixture of compounds of general formula (V):

(V)

[structure with $CH_2R^4$, $X^2$, $Y^2$, $O$, $m$, $n$, $CH_2R^1$, $Y^1$, $X^1$]

wherein $R^1$ and $R^4$ are independently selected from the group consisting of H, methyl, Cl and Br; $X^1$, $X^2$, $Y^1$, $Y^2$ are independently selected from OH, Cl and Br, with the proviso that at least one substituent selected from $X^1$ and $Y^1$ is OH and at least one substituent selected from $X^2$ and $Y^2$ is OH; and n and m are independently 0, 1, 2, 3, 4, 5, 6, 7, 8, 9 or 10;

is reacted with an acid or a base.

9. The process according to claim 8 further comprising obtaining the compound or the mixture of compounds of general formula (V) in a step wherein epichlorohydrin is reacted with but-2-yne-1,4-diol.

10. The process according to claim 9 wherein epichlorohydrin is reacted with but-2-yne-1,4-diol in presence of an acid or a base.

11. The process according to claim 10 wherein epichlorohydrin is reacted with but-2-yne-1,4-diol in presence of an acid.

12. The process according to claim 1 wherein $R^1$ and $R^4$ are Cl.

13. The process according to claim 1 wherein $R^1$, $R^3$, $R^5$ and $R^6$ are independently selected from H and methyl.

14. The process according to claim 1 wherein m is 0.

15. A mixture of compounds of general formula (I):

(I)

[structure with $OR^6$, $CH_2R^4$, Br, $OR^2$, $OR^5$, $m$, Br, $CH_2R^1$, $n$, $OR^3$]

wherein $R^1$ and $R^4$ are independently selected from the group consisting of H, methyl, Cl, and Br; $R^2$, $R^3$, $R^5$ and $R^6$ are independently selected from the group consisting of H, methyl, or ethyl; and n and m are independently 0, 1, 2, 3, 4, 5, 6, 7, 8, 9 or 10; produced by the process of claim 1.

16. A process for the preparation of a flame-retardant blend, the process comprising a step of blending the product of the process according to claim 1 with a further flame-retardant.

17. A process for the preparation of a premix comprising a step of blending the product of the step or the steps according to claim 1 with a blowing agent and optionally one or more further components selected from the list consisting of further polyol compounds, foam stabilizer, further blowing agents, further flame retardants, catalysts, cross-linking agents and surfactants.

18. A process for the preparation of a polyurethane foam comprising a step of reacting the product of the step or the steps according to claim 1 with one or more isocyanate compounds.

19. The process of claim 1, wherein the compound or the mixture of compounds of general formula (III) is reacted with bromine.

* * * * *